United States Patent [19]

Nilaver et al.

[11] Patent Number: 5,200,508
[45] Date of Patent: Apr. 6, 1993

[54] CELL SURFACE ANTIGEN THAT BINDS WITH L6 MONOCLONAL ANTIBODY

[75] Inventors: Gajanan Nilaver; Lawrence Rosenbaum; Edward A. Neuwelt, all of Portland, Oreg.

[73] Assignee: The State of Oregon acting by and through the State Board of Higher Education on behalf of Oregon Health Sciences University, Eugene, Oreg.

[21] Appl. No.: 807,787

[22] Filed: Dec. 12, 1991

Related U.S. Application Data

[63] Continuation of Ser. No. 483,512, Feb. 22, 1990, abandoned, which is a continuation-in-part of Ser. No. 348,048, May 4, 1989, abandoned.

[51] Int. Cl.$^5$ .............................................. C07K 13/00
[52] U.S. Cl. .................................... 530/350; 530/403
[58] Field of Search ................................ 530/350, 403

[56] References Cited

PUBLICATIONS

Land et al., Nature 295:299–303 (1982).
Breslow, Ann. Rev. Biochem. 48:251–274 (1979).
Hellstrom et al. Proc. Nat'l Acad Sci USA 83:7059–63 (1986).
Schlesinger et al. Proc Natl Acad Sci USA 69(11): 3350–54 (1972).

Primary Examiner—Robert J. Hill, Jr.
Assistant Examiner—Shelly J. Guest
Attorney, Agent, or Firm—Klarquist, Sparkman, Campbell, Leigh & Whinston

[57] ABSTRACT

We disclose the discovery and purification of a tumor antigen that binds the mouse monoclonal antibody L6. Immunohistochemical analysis showed that the antigen is expressed on the membrane surface of LX-1 human lung tumor cells, which retain L6 binding activity when intracerebrally xenografted in nude rats. The antigen is also expressed in the cytoplasm of hypothalamic neurons. Inability of oxytocin and vasopressin hormones to block L6 binding showed that the antigenic epitope resides in neurophysin, the carrier protein associated with the two hormones. Porcine neurophysin did block L6 binding to the antigen. Western blot analysis confirmed that L6-immunoreactivity is neurophysin-related. Immunoaffinity chromatography and gel electrophoresis revealed the antigen molecular weight to be 45000 daltons. Amino-terminal sequencing revealed a 21-amino acid homology with the N-terminus of human pro-pressophysin.

11 Claims, 1 Drawing Sheet

Normal Human Pro-pressophysin[a]

C-Y-F-Q-N$^5$-C-P-R-G-G$^{10}$-K-R-A-M-S$^{15}$-D-L-E-L-R$^{20}$-Q-C-L-P-C$^{25}$-G-P-G-G-K$^{30}$-G-R-C-F

LX-1 Tumor Antigen[b]

A-M-S$^{15}$-D-L-E-L-R$^{20}$-Q-(C)-L-P-(C)$^{25}$-G-P-(G)-(G)-K$^{30}$-(G)-R-R-F

Immunogen for YL-3 Antibody[c]

P-R-G-G$^{10}$-K-R-A-M-S$^{15}$-D

[a] Deduced amino acid sequence from human pre-pro-AVP-NP gene (Sausville et al., 1985).

[b] Amino-terminal sequence determined by automated Edman degradation.

[c] Antibody YL-3 was generated to the shown decapeptide which includes the Lys$^{11}$-Arg$^{12}$ cleavage site between vasopressin and vasopressin-neurophysin.

Parentheses indicate tentative amino acid assignments.

FIG. 1

CELL SURFACE ANTIGEN THAT BINDS WITH L6 MONOCLONAL ANTIBODY

ACKNOWLEDGEMENT

This invention was made with government support under the following grants: Public Health Service Grant DK-37205; National Cancer Institute Grant CA-31770; and National Science Foundation Grant BNS-8820600. The government has certain rights in this invention.

CROSS REFERENCE TO RELATED APPLICATION

This application is a continuation of application Ser. No. 07/483,512, filed on Feb. 22, 1990, now abandoned, which is a continuation-in-part of application Ser. No. 07/348,048, filed May 4, 1989, now abandoned.

FIELD OF THE INVENTION

The present invention relates to the discovery and isolation of a tumor-associated antigen capable of binding with a particular monoclonal antibody.

BACKGROUND OF THE INVENTION

Considerable research has been conducted regarding the binding of monoclonal antibodies (mAbs) to tumor-associated cell surface antigens. The preferential expression of tumor antigens by neoplastic cells allows the antigens to be used as diagnostic and therapeutic tools, as discussed generally in Hellström et al., *Accomplishments in Cancer Research*, 1984 Prize Year, General Motors Cancer Foundation (Fortner and Rhoads, eds.), pp. 216-240 (1985); and Reisfeld et al., *Monoclonal Antibodies and Cancer Therapy*, UCLA Symposia on Molecular and Cellular Biology, New Series, Vol. 27 (1985).

Previous research has shown that $IgG_{2a}$ and $IgG_3$ antibody subclasses hold particular promise in tumor therapy since they are capable of mediating antibody-dependent cellular cytotoxicity (ADCC) in the presence of lymphocytes or complement. For example, use of these subclasses of antibodies to mediate ADCC has been demonstrated in human tumor-bearing nude mice and rats, and in human cancer patients as described in Sears et al., *Lancet* 1:762-765 (1982); and Houghton et al., *Proc. Natl. Acad. Sci. USA* 82:1242-1246 (1985).

The present invention involves in part a monoclonal antibody designated as "L6," which is an immunoglobulin type $IgG_{2a}$. The L6 mAb has been shown to bind to a surface epitope of human lung, colon, breast and ovarian carcinomas, as well as melanomas. Hellström et al., *Proc. Natl. Acad. Sci. USA* 83:7059-7063 (1986). Hence, L6 holds particular promise for tumor therapy and diagnosis, particularly since it exhibits the ability to "target" certain cells, including neoplastic cells, and the apparent ability to manifest ADCC oncolytic activity in rodents. *Id.*

The present invention as described herein involves the discovery, isolation, and characterization of a specific antigen to which the L6 monoclonal antibody binds.

SUMMARY OF THE INVENTION

The present invention generally involves the isolation and purification of an antigen to a particular monoclonal antibody. Specifically, a monoclonal antibody known as "L6" has been shown to bind to a tumor-associated antigen expressed on the cell surface of LX-1 human lung tumor cells. L6 also binds to the surfaces of LX-1 tumor cells xenografted into rats. Double-labeling immunohistochemical experiments using vasopressin and oxytocin antisera have confirmed localization of the L6 antigenic epitope in oxytocin and vasopressin-producing neurons of the hypothalamus. In these hypothalamic cells, the epitope appears to be cytoplasmic, in accord with the fact that oxytocin and vasopressin are axonally transported secretory proteins. Western blot analysis confirmed that L6-immunoreactive material on LX-1 tumor cell membranes is neurophysin-related, and that the epitope has an amino acid sequence shared by neurophysins I and II, which are peptides associated with oxytocin and vasopressin, respectively. The information presented herein is useful in the discovery and implementation of methods designed to diagnose and treat carcinoma tissues.

In addition, the L6 antigen on LX-1 cell membranes is restricted to a 45-kd band, where the molecular weight was determined via gel electrophoresis after immunoaffinity chromatography. This band not only immunoreacts with L6, but also with anti-vasopressin and anti-pro-pressophysin antibodies. Amino-terminal sequencing of the 45-kd band revealed a 21-amino acid homology with the N-terminus of human pro-pressophysin, with substitution of an $Arg^{33}$ residue in the LX-1 antigen for $Cys^{33}$ in human pro-pressophysin.

Northern analysis of LX-1 mRNA with a 30-mer to the C-terminus of rat pro-pressophysin revealed a band of about 1000 bp, which is about 250 bp larger than the corresponding hypothalamic mRNA. In situ hybridization of LX-1 tumor-bearing nude rat brain with the same probe revealed specific hybridization in rat hypothalamus and xenografted LX-1 tumor cells. Therefore, LX-1 cells have a pro-pressophysin-like protein, immunoreactive with L6, present specifically in the cell membrane.

It is accordingly an object of the present invention to provide a purified tumor antigen to which the L6 monoclonal antibody binds.

It is another object of the present invention to provide an antibody/antigen system suitable for use in the characterization and treatment of neoplasms.

These and other objects, features and advantages of the present invention will become apparent with reference to the following Detailed Description and drawing.

BRIEF DESCRIPTION OF THE DRAWING

FIG. 1 shows the amino-terminal amino acid sequence of the LX-1 cell surface antigen, along with amino-terminal sequences of normal human pro-pressophysin and YL-3 antibody immunogen.

DETAILED DESCRIPTION

The L6 antigenic epitope within the neurophysin peptide sequence of LX-1 human lung tumor cells was characterized by a number of methods.

L6 monoclonal antibody was produced and found to bind to hypothalamic regions in nude rats bearing LX-1 tumor xenografts. Since systemically administered monoclonal antibodies cannot permeate the junctions between brain capillary endothelial cells, the monoclonal antibodies do not ordinarily enter the brain. This problem was overcome by transiently disrupting the blood-brain barrier (BBB) with intraarterial hyperosmolar agents, as generally described in Neuwelt, *Impact* of the Blood-Brain Barrier. (Vols 1 and 2), Plenum Press, New York (1989).

Characterization methods employed herein included immunohistochemical studies, including double-labeling experiments, serving to help determine the types of cells to which L6 binds and the particular locations in or on such cells exhibiting L6 binding. In addition, Western blot analyses were conducted to further characterize the antigenic entities to which L6 became bound. In addition, Northern analyses and in situ hybridization studies were performed to further characterize the antigen. Finally, amino-acid sequencing was employed on the purified antigen (Edman degradation) to determine the sequence at the amino terminus of purified LX-1 tumor antigen in part for comparison with other antigens somewhat similar to the LX-1 tumor antigen.

The following Examples provide requisite detail regarding the above and other methods used to isolate, purify, and characterize the LX-1 tumor antigen.

EXAMPLE 1

The L6 monoclonal antibody (mAb) is an immunoglobulin type IgG$_{2a}$. It was produced by a hybridoma resulting from the fusion of spleen cells derived from a BALB/c mouse immunized with cultured human lung adenocarcimona cells. Mouse NS-1 myeloma cells (Oncogen, Seattle, Wash.) were used as a fusion partner. The L6 mAb has previously been shown to recognize a cell-surface antigen expressed in human lung, breast, and colon carcinomas. Hellstrom, *Cancer Res.* 46:3917-3923 (1986). Furthermore, the L6 mAb has been shown to induce lysis of L6-antigen-positive human tumor cells in the presence of human lymphocytes or serum as discussed in Hellström et al., *Proc. Natl. Acad. Sci. USA* 83:7059-7063 (1986).

The lung carcinoma cell line LX-1 described herein was established from a human lung carcinoma. The tumor cells were grown in RPMI-1640 medium (GIBCO, Inc., Grand Island, N.Y.).

Male 12-week-old nude rat progeny from National Cancer Institute specimens were intracerebrally inoculated with 10 microliters ($8 \times 10^5$ cells/mL) of LX-1 tumor cells in the right cerebral hemisphere. Ten adult male Long-Evans rats and 5 adult male homozygous Brattleboro rats with diabetes insipidus (HoDI) (weight =approximately 250-300 g) were also studied.

The rats were subsequently anesthetized with sodium pentobarbital (60 mg/kg body weight, i.p.) and perfused via transcardiac puncture with 0.9% saline followed by 4% ice cold buffered paraformaldehyde. The brains were removed and blocked in the coronal plane to include the tumor-bearing region and hypothalamus (in the nude rats) or hypothalmic region (in the Long-Evans and HoDI rats). The pituitary glands of the specimens were also removed for immunocytochemical analysis. Brain and pituitary tissues were post-fixed in 4% paraformaldehyde for 24 hours.

Human hypothalamic tissues used in the tests were obtained at post-mortem and blocked in the coronal plane to include the regions of the supraoptic and paraventricular nuclei (SON and PVN, respectively), and immersion-fixed in ice cold buffered 10% formalin for several days.

A number of immunocytochemistry experiments were performed to elucidate the preferential binding behavior of L6 mAb on particular cells found in the brain. Immunocytochemistry was first performed on cytocentrifuged samples of cultured LX-1 tumor cells smeared on silanated glass slides and on Vibratome-cut sections of rat and human hypothalamic tissues to study the binding behavior of L6 mAb to these cells and tissues. The tumor cells immobilized on the slides were fixed by immersion for 10 minutes in 4% buffered paraformaldehyde. Tumor-bearing regions of nude rat brain and rat/human hypothalamus were sectioned serially at 100 micrometers with a Vibratome (Oxford Instruments, Bedford, Mass.) following adequate fixation. The tumor cells affixed to slides and free floating tissue sections were rinsed in Tris buffer (0.05 $\underline{M}$, containing 0.9% NaCl, pH 7.6). Thereafter, they were immunocytochemically labeled with L6 monoclonal antibodies. The basic labeling techniques used at this stage employed biotinylated protein A and avidin-biotin-peroxidase (ABC, Vector Laboratories, Burlingame, Calif.), as described in Nilaver and Kozlowski, *Techniques in Immunochemistry, Volume 4: Academic Press,* pp. 199-215 (1989).

Specifically, the tissues were incubated with the L6 mAb (50 micrograms/mL, overnight at 4° C.) and sequentially reacted with the biotinylated protein A (Vector Laboratories, Burlingame, Calif.) (1:400 dilution, 45 minutes at room temperature) and the ABC complex (1:1000 dilution, 1 hour at room temperature). The ABC complex was prepared 5 minutes before use by mixing together equal parts of 1:1000 dilutions of the Avidin DH and biotinylated peroxidase reagents provided in a Vectastain ABC kit sold by Vector Laboratories, Burlingame, Calif.

Thereafter, samples were treated with 15 mgm % 3,3'-diaminobenzidine tetrahydrochloride (Sigma Corporation, St. Louis, Mo.). A brown reaction product formed. The tumor cells (on slides) were subsequently dehydrated, treated with xylene, and cover-slipped for histological analysis. The tissue sections were mounted on gelatin-coated slides, dehydrated, treated with xylene, and also mounted under cover slips.

Examination of the treated samples revealed that L6 mAb bound to intracerebrally xenografted LX-1 tumor cells, and in the region of the supraoptic and paraventricular nuclei of the hypothalamus in the nude rat brains. The L6 immunoreactivity with the tumor graft was exclusively confined to the surface of the LX-1 tumor cells. A similar pattern of surface staining was observed in cultured LX-1 cells which were cytocentrifuged onto silanated glass slides prior to immunohistochemical staining.

However, L6 immunoreactivity of hypothalamic supraoptic and paraventricular neurons was localized to the cytoplasm extending into the proximal dendrites and axonal processes. The axonal staining had a "beaded"appearance, and terminated in the posterior lobe of the pituitary gland. An identical pattern of cytoplasmic staining of paraventricular and supraoptic neurons (and their axonal processes) was noted in the human hypothalamus. In addition, immunohistochemistry with polyclonal antiserum to porcine neurophysin (ICN Immunobiologicals, Lisle, Ill.) demonstrated a similar pattern of staining in rat paraventricular and supraoptic neuronal systems. Porcine neurophysin polyclonal antiserum recognizes both oxytocin-neurophysin and vasopressin-neurophysin in rat tissues, and was used at a dilution of 1:1000. These results indicate that the L6 mAb recognizes an antigenic epitope common to both oxytocin- and vasopressin-neurophysins. This finding was supported by the observation that L6-labeled perikarya in rat and human hypothalamus were distributed in both the ventral and dorsal aspects of the supraoptic and central/peripheral regions of the paraventricular systems, respectively.

Immunohistochemistry studies employing double staining with L6 monoclonal antibodies and polyclonal antibodies to vasopressin, oxytocin or their carrier proteins (neurophysins) was performed on selected sections of nude, normal and HoDI rat hypothalamus to determine the precise relationship of L6 immunoreactive neurons to the vasopressin and oxytocin neuronal systems. The vasopressin and oxytocin antisera used in the immunocytochemical procedures discussed below were generated in rabbits, and are described generally in Watson et al., *Science* 216:85-87 (1982).

Selected sections of nude, normal, and HoDI rat hypothalami previously immunoreacted with the L6 mAb were also further immunoreacted for vasopressin, oxytocin, or their carrier proteins (neurophysins). These tissues were incubated with polyclonal antibodies specific to the above-described hormones, employing benzidine dihydrochloride as the alternate chromogen to produce blue labeling for the second antigen.

Examination of double-labeled tissue sections revealed that L6 monoclonal antibodies (mAbs) bind to neurons in both the central and peripheral parts of the paraventricular system, while approximately half of the L6-positive neurons also express vasopressin immunoreactivity. In the supraoptic system, the L6-reactive neurons occupied the dorsal and ventral regions of the nucleus, with only the ventral neurons showing additional immunoreactivity for vasopressin. When adjacent L6-stained hypothalamic sections were incubated with the oxytocin antiserum as the second reactant of the double-labeling technique, the L6-reactive neurons not visualized with the vasopressin antibody were found to express oxytocin immunoreactivity.

Further, immunostaining of HoDI rat hypothalamus showed L6-immunoreactivity in only 50% of paraventricular neurons and supraoptic neurons. This result was consistent with a previous report showing that a single base deletion in the neurophysin coding domain of the HoDI pro-pressophysin gene precludes translation of vasopressin and its associated neurophysin. Schmale, *Nature* 38:705-709 (1984). L6-immunolabeled neurons in HoDI hypothalamus appeared to be localized in the peripheral region of the paraventricular system and dorsal aspect of the supraoptic system. Also, L6-immunoreactivity was found to reside exclusively within the oxytocin-ergic subpopulation of paraventricular and supraoptic neurons.

Next, experiments were conducted to study the effects of pre-absorption of the L6 mAb on the ability of the monoclonal antibody to exhibit preferential binding. Specifically, 10 mL of Affigel-10 washed with 6 volumes of cold distilled water were incubated with porcine neurophysin (final concentration of 15 mg/mL), vasopressin (1 mg/mL) or oxytocin (1 mg/mL) in 10 mL of 0.1 $\underline{M}$ HEPES (pH 7.5) containing 80 mM CaCl$_2$ (buffer A) for 4 hours with end-on-end stirring at 4° C. Any remaining active sites on the gel were blocked by the addition of 1 $\underline{M}$ ethanolamine-HCl (pH 8.0; 0.1 mL/mL gel) for 1 hour while rotating at 4° C. The gel was then washed with buffer A until the OD$_{280}$ reached background levels. Coupling efficiency was determined by quantifying protein concentrations in the wash using methods known in the art and described in Bradford, *Anal. Biochem.* 72:248-254 (1976).

The coupled Affigel-10 was centrifuged at 1200×g in a Sorvall SS-34 rotor for 15 minutes, with the supernatant decanted and discarded. The gel was then incubated with L6 monoclonal antibodies (200 micrograms/mL) overnight while rotating at 4° C. The gel-antibody suspension was then recentrifuged at 1200×g, as described above for 15 minutes and the supernatant (absorbed antibody) decanted for use in Western analysis and immunohistochemistry. The coupled Affigel-10 was regenerated by washing with 10 volumes each of 0.1 $\underline{M}$ glycine (ph 3.0), 25 m$\underline{M}$ Na$_2$HPO$_4$ (pH 8.5), and finally with buffer A.

The pre-absorption test results indicated that solid-phase absorption of L6 mAbs (50 micrograms/mL) with synthetic arginine vasopressin- or oxytocin-conjugated Affigel-10 (80 micrograms/mL) had no effect on hypothalamic immunoreactivity. Pre-absorption of L6 monoclonal antibody with equimolar amounts of Affigel-10 conjugated porcine neurophysins, however, completely eliminated all hypothalamic immunoreactivity.

In addition to the foregoing tests, a Western blot analysis was performed, as described below, to further elucidate the antigens to which the L6 mAb binds.

Protein and polypeptide samples were solubilized in 1 × Laemmli sample buffer and heated to 100° C. for 5 minutes. The samples were then electrophoresed on 12.5% total acrylamide (% T; acrylamide:bisacrylamide; 1:15.5) using the tricine-SDS-PAGE system as described in Schäger et al., *Anal. Biochem.* 166:368-379 (1987). Western blot analysis was performed, as described by Rosenbaum et al., *Anal. Biochem.* 183:250-257 (1989). Briefly after electrophoresis, the resulting gels were renatured by washing 4 × 10 minutes in 50 mM Tris (pH 7.4) containing 20% (v/v) glycerol. The proteins were then electrophoretically transferred to nitrocellulose in 10 mMNaHCO$_3$, 3mM Na$_2$CO$_3$ (pH 10.0), with 20% (v/v) methanol for 1 hour at 1 amp employing a TE-42 Transphor unit (Hoefer, Inc., San Francisco, Calif.).

After drying overnight, the nitrocellulose "blot" was fixed for 4 hours in 0.5% (v/v) paraformaldehyde vapor at 70° C. to immobilize the peptides. Nonspecific binding sites on the blots were blocked with 3% (w/v) gelatin in 20 mM Tris (pH 7.5) with 0.5 $\underline{M}$ NaCl, 0.1% (v/v) Tween-20 and 0.02% (v/v) NaN$_3$ (TTBS) for 1 hour, followed by a 3 × 5 minute wash in TTBS. The blots were then incubated with primary antibody in TTBS with 0.1% (w/v) recrystallized bovine serum albumin for 2-4 hours at room temperature and washed for 3 × 5 minutes in TTBS. Next, the blots were incubated with biotinylated protein A (3 micrograms/mL) in TTBS with 0.1% (w/v) recrystallized bovine serum albumin for 1 hour at 25° C. and washed for 3 × 5 minutes in TTBS. The blots were incubated in ExtrAvidin-alkaline phosphatase (1:3000 dilution) in TTBS for 45 minutes, washed 3 × 5 minutes in TTBS, and transferred to clean trays. Immobilized polypeptide materials were subsequently detected by developing the blots in a mixture of p-nitro blue tetrazolium chloride (0.33 mg/mL) and 5-bromo-4-chloro-3-indolyl-phosphate (0.165 mg/mL) in 0.1 $\underline{M}$ Tris (pH 9.5) containing 0.1 $\underline{M}$ NaCl, 5 mM MgCl$_2$ and 0.5% (v/v) Tween-20. Blots incubated with the F(ab')$_2$ fragment of the L6 monoclonal antibody were reacted with alkaline phosphatase-conjugated goat anti-mouse IgG F(ab')$_2$ (1:500 dilution) for 90 minutes, and washed 3 × 5 minutes in TTBS. They were then developed in p-nitro blue tetrazolium chloride/5-bromo-4-chloro-3-indolyl-phosphate, as described above.

The Western blot analysis indicated that polyclonal anti-porcine neurophysin (which immunoreacts with both neurophysin I and neurophysin II) showed immunoreactivity with processed neurophysin II and neurophysin I, as well as with the precursor peptide pro-pressophysin present in the neurophysin II preparation. The analysis also indicated that L6 mAbs recognize a shared sequence in the two carrier proteins as demonstrated by immunoreactivity with neurophysin II and neurophysin I. These results indicate that L6 recognizes the neurophysin domain of pro-pressophysin and not the C-terminal glycopeptide of pro-pressophysin.

The domain-specific binding of L6 mAb was confirmed by reacting neurophysin II with glycopeptidase F enzyme prior to electrophoresis and immunoblotting with L6 mAb, which did not alter the immunoreactivity. Probing the blot with a mouse monoclonal antibody (P1.17) of a similar class and subtype to L6 (IgG$_{2a}$) did not show binding to either neurophysin II or neurophysin I, thereby demonstrating the specificity of L6 binding to neurophysins.

The specificity of L6 immunoreactivity to the neurophysins was further confirmed by pre-incubating the L6 mAb with neurophysin-bound Affigel-10, and using the supernatant to probe neurophysin II and neurophysin I in the immunoblots. This resulted in elimination of virtually all immunoreactivity for both neurophysin II and neurophysin I.

Northern analysis and in situ hybridization on LX-1 tumor cells were also performed with a synthetic human pro-pressophysin oligonucleotide probe. These studies demonstrated expression of pro-pressophysin mRNA in these cells.

Additional experiments were conducted in order to confirm the presence of pro-pressophysin in cell membranes of LX-1 tumor cells. Identification was made by Western blotting of the L6 mAb affinity-purified LX-1 cell membranes. Thereafter, probing was completed using a polyclonal anti-pro-pressophysin antibody.

Specifically, LX-1 cells (approx. $10^8$) were homogenized in 10mL of 25 mM imidazole (pH 7.4) containing 5 mM EGTA, 1 mM EDTA, 0.02% NaN$_3$, and 0.001 M PMSF. An equal volume of 5% Tween 40 was added and the homogenate centrifuged at 2000 $\times$ g for 10 min. The supernatant was then centrifuged at 100,000 $\times$ g for 1 hour. The resulting pellet was subsequently resuspended to a protein concentration of 1 mg/mL and added to Zwittergent-14 (7 mM) to give a final concentration of 3.5 mM. After incubating 10 min. at room temperature, the solubilized tumor membranes were centrifuged at 100,000 $\times$ g for 1 hour.

Solubilized membranes were incubated with 1/50 volume of a 10% stock solution of *Staphlococcus aureus* for 30 min at 4° C., followed by centrifugation at 100,000 $\times$ g for 30 min. The supernatant was then affinity-purified by batch absorption to L6/protein A-Sepharose crosslinked with 20 mM dimethylpimelimidate. After extensive washing with 50 mM Tris (pH 8.2) containing 0.5 M NaCl, specifically bound antigen was eluted with 50 mMdiethylamine (pH 11.5). Eluted samples were electrophoresed, blotted, and probed.

The results of these identification tests confirmed the specific expression of pro-pressophysin in the LX-1 tumor cell membrane. This indicates that pro-pressophysin is a cell surface antigen to which L6 binds.

The test results described in this Example demonstrate that L6 mAb binds to the surface of intracerebrally xenografted LX-1 tumor cells, and recognizes a common sequence shared by neurophysin I and neurophysin II. In addition, the tests show L6 immunoreactivity in rat and human hypothalamus within the neurons of the supraoptic and paraventricular systems. The hypothalamic immunoreactivity, however, is exclusively cytoplasmic, being confined to neuronal perikarya, their proximal dendrites, and the entire length of their axonal processes.

The test results also show that the L6 mAb recognizes an antigenic epitope common to neurophysin I and neurophysin II, as demonstrated by L6 reactivity within vasopressin and oxytocin-producing neurons of the supraoptic and paraventricular systems by double staining-immunohistochemistry. The inability of both oxytocin and vasopressin to block hypothalamic L6 immunoreactivity implies that the L6 mAb does not recognize either of these nonapeptides. This result was further substantiated by Western blot analysis of synthetic vasopressin and oxytocin with L6 mAb. The selective expression of L6 immunoreactivity in oxytocin neurons of the HoDI rat (which cannot express vasopressin or vasopressin-neurophysin due to a deletion in the pro-pressophysin gene) further indicates that L6 mAb immunoreactivity is neurophysin-related. This is confirmed by the complete elimination of hypothalamic L6 immunoreactivity by pre-absorption of the monoclonal antibody with Affigel-conjugated porcine neurophysin.

The Western blot analysis of purified bovine and human neurophysins with L6 mAb also revealed immunoreactivity in bands corresponding to processed neurophysin I, neurophysin II and pro-pressophysin. The identities of these bands were confirmed by the additional use of antisera to porcine neurophysin, human neurophysin and vasopressin.

The intensity of binding to neurophysin I was significantly less than that observed for neurophysin II, raising the possibility that the L6 mAb preferentially binds to neurophysin II and pro-pressophysin. Since the intensity of pro-pressophysin immunoreactivity is notably less than that of processed neurophysin, reactivity for pro-oxyphysin would not be expected. The results of the glycopeptidase studies noted above which exclude potential cross-reactivity of L6 mAb with the C-terminal glycopeptide domain of pro-pressophysin also preclude preferential L6 binding to pro-pressophysin. In addition, immunohistochemistry demonstrates equal reactivity of L6 mAb with both neurophysin I and neurophysin II, at least in human and rat hyopthalamus. Alternatively, since pro-oxyphysin and processed neurophysin I differ in molecular weight by only 990 daltons, both peptides could migrate as a single broad band under the electrophoresis conditions described herein, precluding the identification of a distinct pro-oxyphysin band when probed with L6 mAb.

Further evidence precludes potential non-specific reactivity of L6 with neurophysins. For example, the P1.17 monoclonal antibody, which is of the identical subclass as L6 mAb, showed no immunoreactivity when used to probe the neurophysin blots. P1.17 also did not demonstrate any staining of LX-1 cells, or of human hypothalamus or rat hypothalamus tissues. Also, when the F(ab')$_2$ fragment of L6 was used to probe human and bovine neurophysin by immunoblots, immunoreactivity with similar intensity to intact L6 mAb was observed. This demonstrates specific binding of the F(ab')2 portion of the L6 mAb molecule to neurophysin since potential non-specific binding at the Fc region was eliminated. In addition, pre-absorption of L6 mAb to Affigel-bound neurophysin virtually eliminated all L6 immunoreactivity for bovine neurophysin I and neurophysin II. To insure that the binding of L6 to Affigel-neurophysin is mediated by a specific antigen-antibody reaction rather than by electrostatic interaction, the L6 mAb was pre-absorbed with poly-L-lysine prior to incubation with the neurophysin-bound Affigel resin. Elimination of electrostatic charge with the basic peptide poly-L-lysine failed to affect L6-neurophysin binding. Finally, the nitrocellulose blots described above were exposed to paraformaldehyde vapor to immobilize and fix the proteins prior to immunoblotting. This procedure inactivated the ε-amino group on lysine residues, and significantly reduced electrostatic interaction.

EXAMPLE 2

In this Example, a neurophysin-like precursor is isolated from the human lung cancer cell line LX-1 and characterized. LX-1 cells do not appear to process or secrete this precursor peptide. Instead, the precursor appears to reside intact in the LX-1 cell membrane.

Extracts from LX-1 cells were immunoprecipitated (a form of immunopurification) by the following procedures:

LX-1 cells were obtained from Mason Laboratories, Worcester, Mass. Two days after passaging, [$^{35}$S]-cysteine was added (1 mCi/$10^8$ cells) to the LX-1 cells and allowed to incubate for 20 hr under normal culture conditions (37° C.; 5% $CO_2$) The $^{35}$S-labeled cells were washed three times in 50 mM $NaH_2PO_4$ (pH 7.5) containing 0.15 $\underline{M}$ NaCl. The labeled LX-1 cells (5 × $10^8$ ceils/mL) were solubiized in a lysis buffer containing 10 mM Tris HCl pH 8.2, 0.15 M NaCl, 1 mM EDTA, $10^{-4}$ $\underline{M}$ PMSF and 0.5% (v/v) Nonidet P-40. After a 15 min incubation on ice, the suspension was centrifuged at 3000 × g for 10 min to remove debris and the supernatant centrifuged at 100,000 × g for 1 hr.

After adjusting the supernatant to 0.5 $\underline{M}$ NaCl, 1/50 volume of 10% formalin-fixed *Staphylococcus aureus* suspension was added (30 min at 4° C.) to remove non-specific binding.

To perform immunoprecipitation, solubilized LX-1 cell extracts (containing approximately 5 × $10^6$ cells/tube) were incubated with YL-3 antibody to PPYsin (at a dilution of 1:500) overnight at 4° C. YL-3 is a polyclonal antibody raised to the decapeptide sequence of human PPYsin shown in FIG. 1. This antibody has been shown to specifically label paraventricular (PVN) and supraoptic (SON) nuclei of monkey and rat hypothalamus by immunohistochemistry and NP precursor in human and bovine pituitary by Western blot analysis. Protein A-Sepharose (50 μL) was then added and allowed to incubate for 30 min at 4° C. After centrifugation in an Eppendorf Microfuge (2 min) to sediment the beads, the pellet was washed sequentially in 50 mM Tris HCl (pH 8.2) containing 0.5 MNaCl, 50 mM Tris HCl (pH 8.2) containing 0.1% (v/v) SDS, and 10 mM Tris HCl (pH 7.4) containing 0.1% (v/v) Nonidet P-40. The washed pellet was then boiled for 2 min in 1X Laemmli sample buffer containing 25 mM DTT, centrifuged, and the supernatants electrophoresed. Laemmli sample buffer is described in Laemmli, *Nature (London)* 227:680–685 (1970).

SDS-polyacrylamide gel electrophoresis of the extracts was performed, as described by Laemmli (*supra*), using 12.5% fixed acrylamide (acrylamide:bisacrylamide; 1:30). Gels were stained with Coomassie blue or with silver according to the method of Heukenshoven and Dernick, *Electrophoresis* 6:103–112 (1985).

Cell membranes solubilized in 0.5% (w/v) Nonidet P-40 resulted in many bands when electrophoresed and stained with Coomassie blue. Since the cell-membrane extract demonstrated relatively weak immunoreactivity when blotted and probed with various antibodies, specific tumor antigen was isolated from the extract using an L6-immunoaffinity column eluted with 50 mM diethylamine at pH 11.5. The neutralized sample was then electrophoresed, resulting in a band corresponding to a $M_r$ of approximately 45,000 by silver staining.

A much less intense band with an apparent $M_r$ of approximately 42,000 appeared to co-purify with the 45 kd protein. This band may be a proteolytic fragment of the $M_r$ 45,000 polypeptide, although it did not appear to be immunoreactive with the antibodies used in this study. Immunoblots were then performed on the 45 kd fragments according to Rosenbaum et al., *Anal. Biochem.* 183:250–257 (1989).

The 45 kd fragment was highly immunoreactive with the antibody YL-3 raised against human PPYsin. Since this antibody only reacts with an intact Lys-Arg cleavage site in PPYsin, the immunoreactivity of YL-3 with the 45 kd fragment strongly suggests that the L6-isolated LX-1 surface antigen is related to PPYsin. The L6 mAb bound to the antigen, while a mAb of the same sub-type L6 (IgG$_{2a}$), P1.17 (Oncogen, Seattle, Wash.), failed to show any immunoreactivity. The ability of the 45 kd band to bind a polyclonal antibody to vasopressin confirmed that the 45 kd fragment was a pro-pressophysin-related protein. Polyclonal antibodies to processed NP and oxytocin (OT) failed to demonstrate immunoreactivity with the purified antigen.

Since Example 1 demonstrated L6 immunoreactivity to be exclusively confined to the surface of LX-1 tumor cells, the LX-1 antigen was further characterized by Western blot analysis and immunoprecipitation with anti-human pro-pressophysin. In these analyses, samples were electrophoresed, blotted, and probed as described above.

To purify the LX-1 antigen, L6 was covalently cross-linked to protein A-Sepharose (12 mg antibody/mL gel) with dimethylpimelimidate (20 mM) to form an L6/protein A affinity matrix essentially as described by Schneider et al., *J. Biol. Chem.* 257:10766–10769 (1982). After eliminating non-specific binding from LX-1 cell extract using *S. aureus* as described above, the extract was centrifuged at 100,000 × g for 30 min and the supernatant added to the L6/protein A affinity matrix. After rotating gently overnight at 4° C., the protein A-Sepharose was pelleted at 500 × g for 2 min and washed with 50 mM Tris HCl (pH 8.2) containing 0.5 $\underline{M}$ NaCl, 1 mMEDTA and 0.5% (v/v) Nonidet P-40, followed by washes in 50 mM Tris HCl (pH 8.2) containing 0.15 $\underline{M}$ NaCl, until the $A_{280}$ was reduced to a background level. Specifically bound antigen was eluted twice with an equal volume of 50 mMdiethylamine, pH 11.5. The pooled elutions were immediately neutralized by adding 1/10 volume 0.5 $\underline{M}NaH_2PO_4$.

The LX-1 membrane antigen was found to react strongly with YL-3 in the Western blot, revealing a band with an approximate $M_r$ of 45,000. The LX-1 cytosolic extract showed only a very faint band at 45 kd and a slight band at 23 kd when probed with YL-3. YL-3 also reacted with normal PPYsin ($M_r$ 23,000). Since the total protein in the cytosol extract tested was 100 times more than the total protein in the membrane extract, it was concluded that the vast majority of LX-1 antigen resides in the cell membrane, not in the cytosol. The culture medium, furthermore, was negative for immunoreactivity with anti-VP, anti-NP, YL-3, and L6 mAb by Western blot analysis. The serum from tumor-bearing nude rats also showed no increase in VP levels by radioimmunoassay (RIA) when compared to control nude rats. RIA was performed according to Morton et al., *J. Endocrinol.* 65:411–424 (1975).

LX-1 cells were also surface-iodinated using lactoperoxidase (50 μg/mL), glucose oxidase (25 μg/mL), and Na $^{125}$I (1 mCi/$10^8$ cells). The reaction was initiated with the addition of glucose (250 μg/mL), allowed to incubate for 20 min at room temperature, and terminated with KI (0.4 mg/mL). The $^{125}$I labeled cells were washed three times in 50 mM NaH$_2$PO$_4$ (pH 7.5) containing 0.15 M NaCl, and solubilized as described above. Subsequent antigen binding of the solubilized extract with YL-3 further demonstrated membrane localization of the LX-1 antigen. These results confirm the non-secretory nature of LX-1 cells, and the preferential targeting of propressophysin-related protein to LX-1 cell membranes.

A potential explanation for the observed high molecular weight of the PPYsin-like LX-1 antigen is a high degree of glycosylation, altering mobility on the gel, or dimerization of the normal 23 kd protein. To address these possibilities, purified LX-1 tumor antigen was digested with glycopeptidase F, blotted and probed with YL-3 antibody. This resulted in a weak immunoreactive band with a $M_r$ of approximately 35,000 and the complete elimination of the 45 kd band. Additionally, when cultured LX-1 tumor cells were incubated with [$^{35}$S]-cysteine and immunoprecipitated with YL-3, a 45 kd band was seen, corresponding to the purified antigen. A higher molecular weight band of approximately 57 kd was also detected, which could represent a pre-pro form of the polypeptide, or a larger, less processed 45 kd protein. These studies suggest that the 45 kd band is not the result of dimerization or excessive glycosylation, but rather, a unique form of pro-propressophysin.

Next, amino-acid sequencing was performed on the LX-1 tumor antigen to compare with the sequence of normal human PPYsin and the immunogen for the YL-3 antibody. The sequencing procedure was as follows: Nondenatured immunoaffinity-purified LX-1 antigen (150 pmols) was subjected to limited proteolysis with carboxypeptidase B (0.6 μg) in 0.3 mM N-ethylmorpholine acetate (pH 8.5) for 5 hrs at 37° C. The reaction was quenched by adding acetic acid to pH 3.0. Samples were then electrophoresed as described above, and electroblotted onto Immobilon PVDF membranes (Millipore Corp., Bedford, Mass.) according to Matsudaira, *J. Biol. Chem.* 262:10035–10038 (1987). Membranes were stained briefly in 0.1% (w/v) Coomassie blue R-250, destained, and the band excised. The stained protein band was sequenced by automated Edman degradation in a gas-phase sequencer (Model 470A, Applied Biosystems, Inc., Foster City, Calif.) equipped with a Applied Biosystems, Inc. 120A PTH analyzer. Approximately 60 pmol of LX-1 antigen was sequenced based on the yield of identified alanine.

FIG. 1 summarizes the results of the sequence analysis. Initial attempts to sequence the immunoaffinity-purified LX-1 antigen from HPLC fractions in acetonitrile or directly from protein electroblotted onto PVDF membranes were unsuccessful due to N-terminal blockage. In order to circumvent this, the protein was subjected to limited proteolysis with carboxypeptidase B (Sigma, St. Louis, Mo.) containing a trace amount of trypsin. Automated Edman degradation of the cleaved antigen electroblotted onto PVDF membranes revealed a sequence with a 21 amino acid homology (including tentative assignments) with the N-terminal portion of human PPYsin (see FIG. 1). A major deviation between the two sequences is the substitution of an Arg$^{33}$ residue in the LX-1 tumor antigen in place of Cys$^{33}$ in human PPYsin. This change may have profound effects on the three-dimensional structure of the protein. The sequence analysis, nevertheless, confirmed the identity of the mAb L6-isolated tumor antigen as PPYsin-like.

In order to further characterize the expression of pro-pressophysin-like protein (PPLP) in LX-1 tumor cells, oligonucleotides directed to the C-terminal region of human and rat PPYsin were used in Northern and in situ hybridization analyses.

To perform in situ hybridization, rats were anesthetized with sodium pentobarbital (50 mg/kg body wt, i.p.) and perfused transcardially with saline followed by buffered 10% formalin. The brain was removed, and cryoprotected with 30% (w/v) sucrose containing 0.02% (v/v) diethylpyrocarbonate (DEPC). Cryostat sections (10 μm) where cut in the coronal plane to include the tumor bearing region and hypothalamus, and were mounted on silanated glass slides. In situ hybridization was performed with oligonucleotide probes employing the technique of Davis et al., *Proc. Nat. Acad. Sci. USA* 83:1145–1149 (1986). Sections were delipidated (through progressively graded alcohols and chloroform) and rehydrated (through regressively graded alcohols) to 2 × SSC. Sections were then prehybridized (1 hr, 25° C.) with 2 × SSC containing 50% (v/v) deionized formamide, 10 × Denhardt's solution, 0.1% (v/v) SDS, and 0.1% (w/v) salmon sperm DNA (hybridization buffer). Sections were then overlayed with hybridization buffer containing oligonucleotide probes $^{35}$S-labeled at the 3' end (2.0 × $10^5$ cpm in 30 μL) and 0.1 M of DTT (24 hrs, 25° C.). The sections were then rinsed in 2 × SSC (4 hrs, 25° C., with 15 min changes), air dried, exposed to Hyperfilm β-max (Amersham, Arlington Heights, Ill.) or dipped in Kodak emulsion (NTB-3). After two weeks, the sections were developed, counter-stained, dehydrated, and coverslipped for microscopic analysis.

Specificity of the oligonucleotide probes used in the study were previously confirmed by Northern analysis (see below). Sequence homology between the rat and human PPYsin in the 30-mer region of the rat probe allows detection of both rat and human PPYsin mRNA. The 50-mer human oligonucleotide probe, in contrast, recognizes a unique domain in the human sequence, and consequently should only hybridize with the human PPYsin. The following additional controls were performed to minimize the possibility of a false-positive signal: (i) prehybridization RNAse treatment of tissue; (ii) blocking cDNA-mRNA hybridization by addition of excess unlabeled probe.

The Northern analyses were performed as follows: Total RNA was prepared by homogenizing tissue or cells in 5 M guanidine isothiocyanate and precipitated with 4 M LiCl as described by Cathala et al., *DNA* 2:329–335 (1983). Poly(A+) RNAs were isolated using the oligo(dT)-cellulose batch method described by Sherman et al., *J. Neurosci.* 6:1685-1694 (1986). Samples were fractionated on standard 1.5% agarose formaldehyde gels and passively transferred to nylon membranes in 20 × SSC. Membranes were prehybridized overnight at 45° C. in 5 × SSC/20 mM NaH$_2$PO$_4$, pH 7.5, containing 20% (v/v) deionized formamide, 5 × Denhardt's solution (1% [w/v] polyvinylpyrrolidone, M$_r$ 40,000; 1% [w/v] Ficoll, M$_r$ 400,000; and 1% [w/v] BSA), 0.1% (v/v) SDS and 10 µg/mL sonicated, heat denatured salmon sperm DNA. Filters were then hybridized (24 hrs; 45° C.) in a similar buffer containing 1 × Denhardt's solution plus 1.0 µg/mL salmon sperm DNA and 4 nM 30-mer oligonucleotide $^{32}$P-labeled at the 3'-end to a specific activity of 5-8 × 10$^8$ dpm/nmol. Oligonucleotides were labeled on the 3' end with terminal deoxynucleotidyl transferase, and purified as described by Davis et al. (eds.) *Basic Methods in Molecular Biology* (Elsevier, N.Y.) (1986). Membranes were washed to a stringency of 2 × SSC containing 1% (v/v) SDS at 45° C. and exposed to x-ray film.

In situ hybridization of nude rat brain bearing LX-1 tumor xenografts with the 30-mer oligonucleotide probe to rat PPYsin demonstrated specific hybridization signal within vasopressin-ergic neurons in the SON and PVN nuclei of rat hypothalamus. Autoradiographic grains were also localized in the intracerebral human tumor xenograft, confirming expression of vasopressin mRNA in the LX-1 tumor cells. When serial adjacent sections of tumor-bearing nude rat brain were hybridized with the 50-mer oligonucleotide probe to human PPYsin, the hybridization signal was confined to the human tumor xenograft, with no labeling being detected within vasopressin-ergic neurons of the rat hypothalamus. These studies confirmed the stringency of hybridization as well as the specificity of the human and rat PPYsin probes used in the experiments.

Parallel experiments with the 30-mer rat and 50-mer human synthetic pro-oxyphysin probes, performed on adjacent sections of tumor bearing nude rat brain, failed to demonstrate presence of oxytocin mRNA in the LX-1 tumor xenografts. The presence of in situ signal within oxytocin-ergic neurons of the rat SON and PVN in sections probed with the 30-mer rat probe confirmed the stability of tissue mRNAs and the hybridizing specificity of the probe used. The absence of signal in corresponding hypothalamic regions of sections probed with the 50-mer human probe served to further validate the specificity of hybridization.

When rat hypothalamic total RNA was probed with the [$^{32}$P]-labeled rat 30-mer, a strong signal was observed corresponding to a message size of 750 bp. Total RNA from rat cerebellum did not reveal hybridization with the rat 30-mer probe. When poly (A+)RNA isolated from LX-1 tumor cells was probed with the rat 30-mer, a band corresponding to a message size of approximately 1000 bp was observed. This message is approximately 250 bp larger than the reported size of normal PPYsin mRNA. This may, in part, account for the high molecular weight of pro-pressophysin-like protein (PPLP) in the tumor membrane. Both the in situ hybridization and Northern analysis suggest the selective expression of VP mRNA in LX-1 human tumor xenografts and in cultured cells.

The identification of the antigen to which the L6 monoclonal antibody binds has diagnostic and therapeutic usefulness. For example, the L6 monoclonal antibody may be used as a therapeutic vehicle on which a desired antineoplastic agent is bound for selective delivery by the mAb to a neoplastic locus in the body. For treating brain tumors, the blood-brain barrier would first be opened using a chemical agent such as manitol or glycerol, followed by administration of the antineoplastic conjugated to the L6 mAb. The L6 mAb can also be combined with a diagnostic imaging agent to aid in cancer diagnosis and localization.

The L6 mAb may also be used to study the in vivo production and function of pro-pressophysin and pro-oxyphysin in animal, as well as human central nervous systems.

In addition, in the case secretory tumors, the L6 mAb and other newer-generation mAbs to the LX-1 tumor antigen might also be used in a serum diagnostic test. A conjugated L6 mAb would be given to patients as either a diagnostic or therapeutic agent to identify and localize tumor cells in the body. A possible concern with this approach involves the reaction of the mAb with circulating neurophysin. However, preliminary tests indicate that these problems do not occur to any substantial degree, even with doses of over one gram per patient.

A further possible application of the L6 antibody is the use of a clone of the LX-1 tumor antigen as part of an immunotherapy regimen. The application of such a cloned antigen would be very significant since lung, breast, colon, and ovarian cancer (all of which react with L6) are four of the most common forms of cancer. For example, the LX-1 antigen or a cloned gene for the LX-1 antigen placed in a viral vector could be administered as a vaccine for active immunotherapy.

Having illustrated and described the principles of the present invention with reference to detailed examples, it should be apparent to those of ordinary skill in the art that the invention may be modified in arrangement and detail without departing from such principles. We claim as our invention all such modifications as come within the true spirit and scope of the following claims.

We claim:

1. A tumor antigen having characteristics comprising:
   (a) being a glycoprotein normally present on cell membranes of LX-1 human lung carcinoma cells; and
   (b) a purity sufficient to yield, when the tumor antigen is electrophoresed on an SDS/polyacrylamide gel, a single band migrating to a position in the gel corresponding to a molecular weight of about 45 kilodaltons, the band immunoreactive with YL-3 polyclonal antibodies and with L6 monoclonal antibodies.

2. A tumor antigen as recited in claim 1 with which L6 monoclonal antibodies are immunoreactive after said monoclonal antibodies have been pre-absorbed with vasopressin.

3. A tumor antigen as recited in claim 1 with which L6 monoclonal antibodies are immunoreactive after said monoclonal antibodies have been pre-absorbed with oxytocin.

4. A tumor antigen as recited in claim 1 with which L6 monoclonal antibodies do not immunoreact after said monoclonal antibodies have been pre-absorbed with porcine neurophysins.

5. A tumor antigen having a purity sufficient to yield, when the tumor antigen is electrophoresed on an SDS/polyacrylaminde gel, a single band migrating to a position in the gel corresponding to a molecular weight of about 45 kilodaltons, the band being immunoreactive with anti-propressophysin antibodies and with L6 monoclonal antibodies, and having an amino-terminus amino-acid sequence of A-M-S$^{15}$-D-L-E-L-R$^{20}$-Q-(C)-L-P-(C)$^{25}$-G-P-(G)-(G)-K$^{30}$-(G)-R-R-F.

6. A tumor antigen as recited in claim 5 wherein said amino-terminal amino-acid sequence comprises a portion of the amino-acid sequences of neurophysin I and neurophysin II.

7. A tumor antigen as recited in claim 5 having an antigenic epitope selected from the group consisting of neurophysin I, neurophysin II, and pro-pressophysin.

8. A tumor antigen as recited in claim 5 which is a glycoprotein.

9. A tumor antigen as recited in claim 5 immunoreactive with YL-3 antibodies.

10. A tumor antigen as recited in claim 5 synthesized by LX-1 human lung carcinoma cells.

11. A tumor antigen as recited in claim 10 synthesized by LX-1 cells from an LX-1 mRNA exhibiting a band of about 1000 bp when subjected to Northern analysis with a 30-mer to the C-terminus of rat propressophysin.

* * * * *